United States Patent
Ishiura et al.

(10) Patent No.: US 7,099,002 B2
(45) Date of Patent: Aug. 29, 2006

(54) DEFECT DETECTOR AND METHOD OF DETECTING DEFECT

(75) Inventors: Tomoaki Ishiura, Susono (JP); Kunihiko Miyazaki, Numazu (JP); Katsumi Ichifuji, Hamamatsu (JP)

(73) Assignee: Ricoh Company, Ltd., Tokyo (JP)

( * ) Notice: Subject to any disclaimer, the term of this patent is extended or adjusted under 35 U.S.C. 154(b) by 126 days.

(21) Appl. No.: 10/175,906

(22) Filed: Jun. 21, 2002

(65) Prior Publication Data

US 2002/0196432 A1   Dec. 26, 2002

(30) Foreign Application Priority Data

Jun. 21, 2001 (JP) .............................. 2001-188191
May 20, 2002 (JP) .............................. 2002-144016

(51) Int. Cl.
*G01N 21/88* (2006.01)
(52) U.S. Cl. ................................... 356/237.2
(58) Field of Classification Search ........ 356/429–431, 356/237.2–237.3, 612, 600
See application file for complete search history.

(56) References Cited

U.S. PATENT DOCUMENTS

| | | | | |
|---|---|---|---|---|
| 3,792,930 A | * | 2/1974 | Obenreder | 356/445 |
| 3,975,102 A | * | 8/1976 | Rosenfeld et al. | 356/613 |
| 4,865,445 A | * | 9/1989 | Kuriyama et al. | 356/73 |
| 5,825,499 A | * | 10/1998 | Biedermann | 356/394 |
| 5,940,175 A | * | 8/1999 | Sun | 356/237.3 |
| 6,046,803 A | * | 4/2000 | Toh | 356/237.2 |
| 6,196,127 B1 | | 3/2001 | Yamamoto et al. | |

FOREIGN PATENT DOCUMENTS

| | | | |
|---|---|---|---|
| JP | 7-55710 | * | 3/1995 |
| JP | 7-110305 | | 4/1995 |
| JP | 07-128240 | | 5/1995 |
| JP | 07-128241 | | 5/1995 |
| JP | 09-325120 | | 12/1997 |
| JP | 10-206335 | | 8/1998 |
| JP | 2000-137004 | | 5/2000 |
| WO | WO 96/39619 | | 12/1996 |

OTHER PUBLICATIONS

Patent Abstracts of Japan, JP 7-128240, May 19, 1995.
Patent Abstracts of Japan, JP 62-038348, Feb. 19, 1987.

* cited by examiner

*Primary Examiner*—Richard A. Rosenberger
(74) *Attorney, Agent, or Firm*—Oblon, Spivak, McClelland, Maier & Neustadt, P.C.

(57) ABSTRACT

A defect detector having: a first optical system including a first light source to irradiate a surface of a subject with coaxial incident-light while scanning, and a first imaging device to receive light regularly reflected from the subject and change the light to a first electrical signal to form a first electrical image; a second optical system including a second light source to irradiate the surface of the subject with inclined light while scanning, and a second imaging device to receive light scattered at the subject and change the light to a second electrical signal to form a second electrical image, in which the inclined light of the second light source does not meet the coaxial incident-light of the first light source; and a computer to compare the first electrical signal with a predetermined first threshold to detect a concavo-convex defect on the surface of the subject, and to compare the second electrical signal with a predetermined second threshold to detect a blocky color defect on the surface of the subject.

10 Claims, 6 Drawing Sheets

DEFECT DETECTOR AND METHOD OF DETECTING DEFECT

CROSS-REFERENCE TO RELATED APPLICATIONS

This application is related to and claim priority, under 35 U.S.C. §119, from Japanese Patent Application No. 2001-188191, filed in the Japanese Patent Office on Jun. 21, 2001, the entire contents of which are hereby incorporated by reference herein.

BACKGROUND OF THE INVENTION

1. Field of the Invention

The present invention relates to a defect detector and a method of detecting a defect and more particularly, to a defect detector for inspecting a surface of an electrophotographic photoreceptor used for copiers, printers, and facsimiles.

2. Discussion of Background

In processes of manufacturing electrophotographic photoreceptors used for copiers, printers, and facsimiles, the photoreceptors occasionally have defective surfaces such as scratches, foreign materials, and coating irregularities. As a method of detecting the defects, a visual inspection is typically performed by an inspector. However, since the visual inspection has fluctuations due to individual differences among inspectors, various automatic detecting methods and apparatus have been suggested.

For example, as a prior art apparatus and method, Japanese Laid-Open Publication No. 9-325120 (hereinafter referred to as a Prior Example 1) discloses a detector detecting the following defects by irradiating an electrophotographic photoreceptor from a light source, receiving light reflected from the photoreceptor with a camera, and producing an electrical signal representing the difference between:

(1) a concavo-convex defect having a high rate of change of surface concavity and convexity, such as pin holes, dents, coating scratches, and dusts; and (2) a blocky defect having a low rate of change of surface concavity and convexity, such as coating irregularities of the photosensitive layers.

In addition, Japanese Laid-Open Publications Nos. 7-128240(hereinafter referred to as a Prior Example 2) and 7-128241(hereinafter referred to as a Prior Example 3) disclose a detector taking plural photographs of a concavo-convex defect and a blocky defect with a light source and plural charge coupled device (hereinafter "CCD") cameras or a CCD camera and plural light sources.

However, in an optical system of the Prior Example 1, both the concavo-convex defect and the blocky defect are photographed without distinction, and a decision to pass or fail has to be made in accordance with the defect having a severer acceptance criterion. Therefore, even a normally good photoreceptor is disposed of as a defective one, or a photoreceptor, which the defect detector judges to be rejected, has to be inspected again by an inspector. In addition, there is an advantage that the optical system is easily controlled because of its few controllers, but there is a disadvantage that when sensitivity of photographing either the concavo-convex defect or the blocky defect is increased, sensitivity of photographing the other defect is decreased.

Further, in the Prior Examples 2 and 3, two light sources or two CCD cameras can increase sensitivities of photographing both the concavo-convex defect and the blocky defect. However, inspection time is long because of its plural times of photographing. In addition, the control operation is complicated because plural CCD cameras are combined with a light source or plural light sources are combined with a CCD camera.

Because of these reasons, a need exists for a defect detector which can efficiently detect a concavo-convex defect and a blocky defect by photographing a defect having a high rate of change of surface concavity and convexity and a defect having a low rate of change thereof with separate optical systems, and which can reduce losses due to excessive inspections.

SUMMARY OF THE INVENTION

Accordingly, an object of the present invention is to provide a defect detector capable of efficiently detecting a concavo-convex defect and a blocky defect by photographing a defect having a high rate of change of surface concavity and convexity and a defect having a low rate of change thereof with separate optical systems, and which can reduce losses due to excessive inspections. In addition, another object of the present invention is to provide a method of detecting a defect.

Briefly this object and other objects of the present invention, as hereinafter will become more readily apparent, can be attained by a defect detector having a first optical system including: a first light source to irradiate a surface of a subject with coaxial incident-light while scanning, and a first imaging device configured to receive light regularly reflected from the subject and change the light to a first electrical signal to form a first electrical image; a second optical system including a second light source to irradiate another point of the surface of the subject with inclined light while scanning, and a second imaging device to receive light scattered at the subject and change the light to a second electrical signal to form a second electrical image; and a computer to compare the first electrical signal with a predetermined first threshold to detect a concavo-convex defect on the surface of the subject, and to compare the second electrical signal with a predetermined second threshold to detect a blocky color defect on the surface of the subject.

These and other objects, features and advantages of the present invention will become apparent upon consideration of the following description of the preferred embodiments of the present invention taken in conjunction with the accompanying drawings.

BRIEF DESCRIPTION OF THE DRAWING FIGURES

Various other objects, features, and attendant advantages of the present invention will be more fully appreciated as the same becomes better understood from the detailed description when considered in connection with the accompanying drawings in which like reference characters designate like corresponding parts throughout and wherein.

DETAILED DESCRIPTION OF THE PREFERRED EMBODIMENTS

Generally, the present invention provides a defect detector having: a first optical system including a first light source to irradiate a surface of a subject with coaxial incident-light while scanning, and a first imaging device configured to receive light regularly reflected from the subject and change the light to a first electrical signal to form a first electrical image; a second optical system including a second light source to irradiate another point of the surface of the subject with inclined light while scanning, and a second imaging device to receive light scattered at the subject and change the light to a second electrical signal to form a second electrical image; and a computer to compare the first electrical signal with a predetermined first threshold to detect a concavo-convex defect on the surface of the subject, and to compare the second electrical signal with a predetermined second threshold to detect a blocky color defect on the surface of the subject.

Accordingly, an accurate decision to pass or fail can be made because the concavo-convex defect and the blocky color defect of the subject can be detected with separate optical systems and judged with an algorithm in accordance with each defect.

Figure 1:
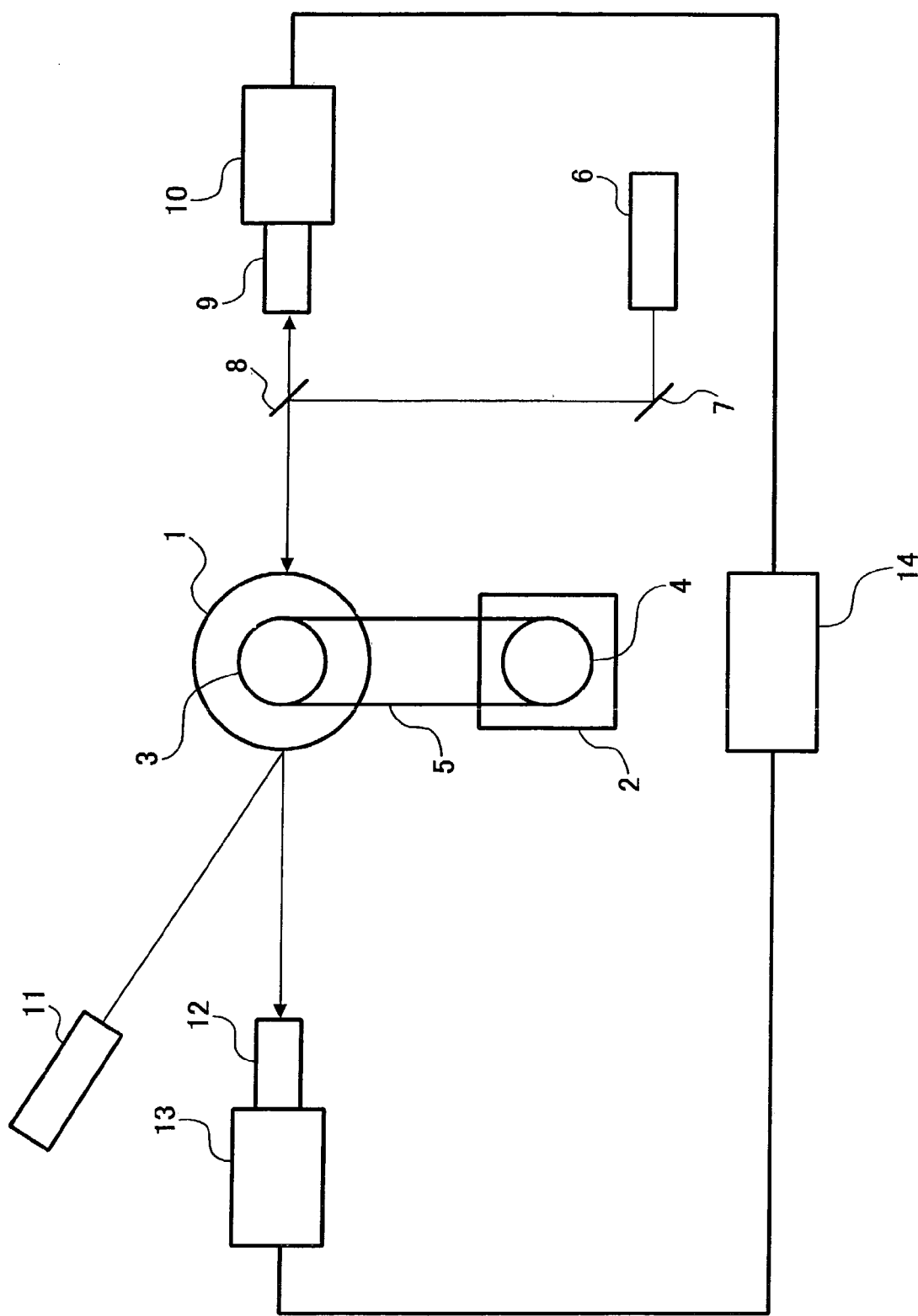
FIG. 1 is a schematic view illustrating an embodiment of the defect detector of the present invention.

FIG. 1 is a schematic view illustrating an embodiment of the defect detector of the present invention. In FIG. 1, a subject 1 is, for example, an electrophotographic photoreceptor including an undercoat layer, a charge generation layer, and a charge transport layer sequentially formed on an aluminium substrate having a diameter of 30 mm, a length of 340 mm, and a thickness of 0.8 mm.

The defect detector of the present embodiment includes: a drive unit 2; a driven pulley 3 coaxially fixed with the subject 1; a drive pulley 4 of the drive unit 2; a tension belt 5 rotating the subject 1 at 60 rpm; a light source 6 emitting coaxial incident-light; a total reflection mirror 7 totally reflecting the light emitted from the light source 6; a half mirror 8; a photo acceptance lens 9 collecting light reflecting from the subject 1 through the half mirror 8 to an one-dimensional CCD camera 10 being a monochrome 256 tone one-dimensional CCD camera for changing the reflected light in a normal direction into an electrical signal; a linear light source 11 emitting inclined light; a photo acceptance lens 12 collecting the scattered light from the subject 1 to an one-dimensional CCD camera 13 being a monochrome 256 tone one-dimensional CCD camera for changing the scattered light into an electrical signal; and a computer 14 for comparing the electrical signals transferred from each one-dimensional CCD camera 10 and 13 with predetermined thresholds to binarize the signals and for judging whether there is a defect on the surface of the subject 1.

Next, the operation of this embodiment of the defect detector will be explained.

The light emitted from the light source 6 is reflected by the total reflection mirror 7 to the half mirror 8. The light is further reflected by the half mirror 8 to the surface of the subject 1 which is being rotated by the rotating drive of the drive unit 2 in a normal direction. The reflected light from the surface of the subject 1 is transmitted through the half mirror 8 to the monochrome 256 tone one-dimensional CCD camera 10 through the photo acceptance lens 9 to be changed into an electrical signal. On the other hand, the linear light source 11 located in an inclined position at a predetermined angle of, e.g., 30°, in a normal direction of the subject 1 emits light thereto. The light reflected from the surface of the subject 1 being rotated by the rotating drive of the drive unit 2 is received by the monochrome 256 tone one-dimensional CCD camera 13 through the photo acceptance lens 12 located in a position not to receive the light regularly reflected from the subject 1 to be changed into an electrical signal. Then, the electrical signals changed by the one-dimensional CCD camera are transferred to the computer 14 where the electrical signals are determined to pass or fail.

Figure 5A:
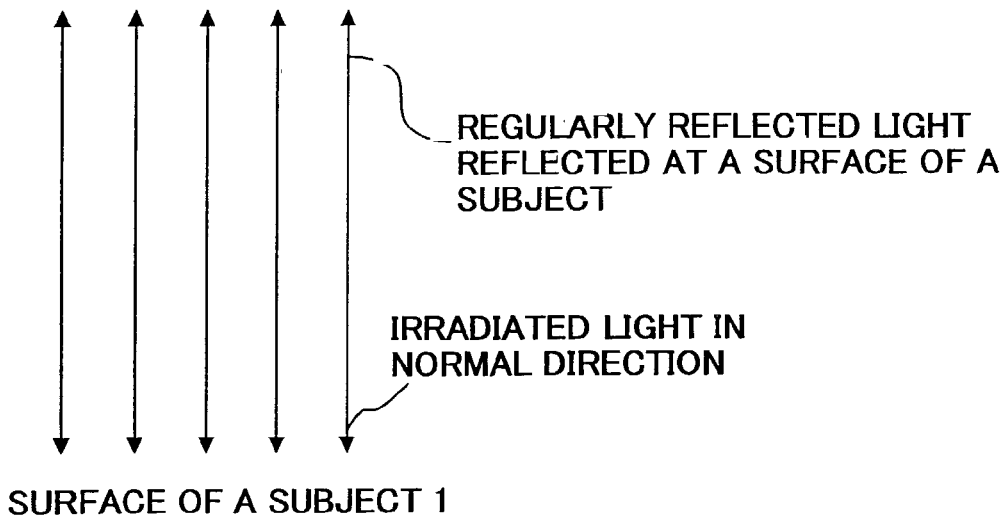
FIG. 5 is a schematic view illustrating an embodiment of the emitted and reflected light direction of the present invention for detecting a concavo-convex defect.
Figure 5B:
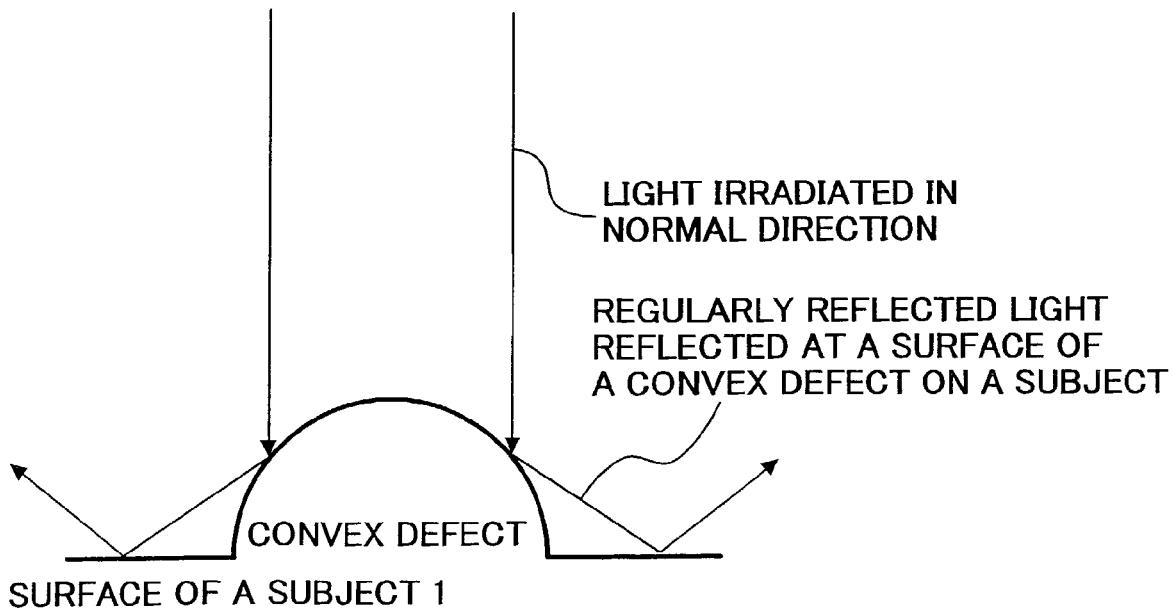

A defect photographed by the optical system using the coaxial incident-light, i.e., a defect inspected based on the electrical signal from the CCD camera 10, is a concavo-convex defect on the surface of the subject 1. As shown in FIG. 5, the light emitted to the subject 1 in a normal direction is mostly reflected in the normal direction if the surface of the subject 1 is normal. However, as shown in FIG. 5, when there is a concavo-convex defect on the surface of the subject 1, the reflection angle is changed and the light is reflected in other directions, i.e., directions other than the direction of the CCD camera 10. Therefore, the photograph of the part of the concavo-convex defect is darker than that of a surrounding normal part. Namely, the total value of the average value of the photographed image density and a predetermined density difference value within a normal limit is a threshold, and by binarizing, a normal part can be changed to 1 (white) and a defective part can be changed to 0(black). Thus, a defective part can be specified. A specified defective area, i.e., the number of parts whose image data are 0 are counted to determine the scale of the defect, and a decision to pass or fail is made by comparing a threshold corresponding to a predetermined standard value of the scale of the concavo-convex defect.

Figure 6:
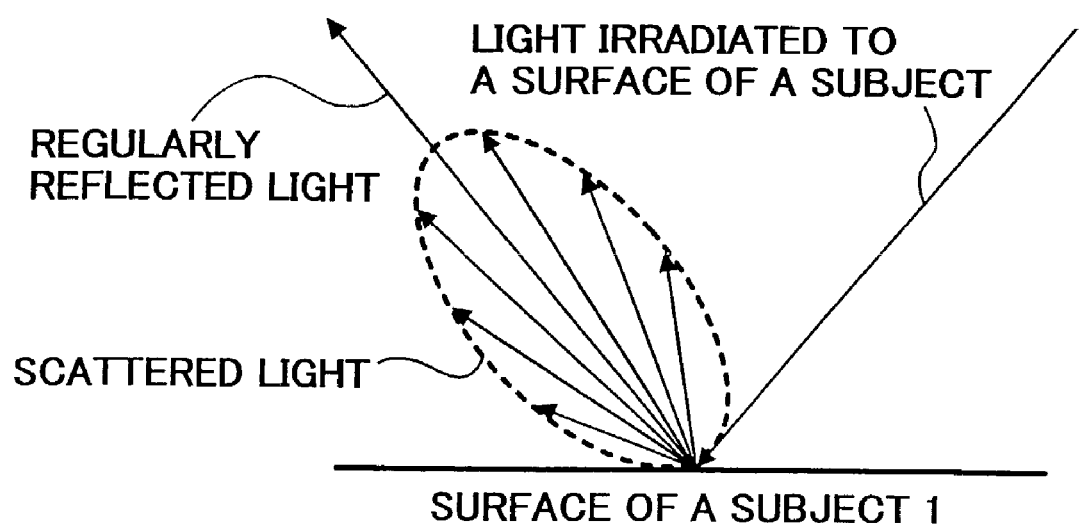
FIG. 6 is a schematic view illustrating an embodiment of the emitted and reflected light direction of the present invention for detecting a blocky color defect.

In addition, a defect photographed by the optical system using the inclined light, i.e., a defect inspected based on the electrical signal from the CCD camera 13, is a blocky color defect on the surface of the subject 1. As shown in FIG. 6, the light emitted to the surface of the subject 1 in a normal direction at an angle of, e.g., 30°, is regularly reflected at the same angle as the incident angle, and at the same time, diffusely reflected in all directions. Both the regularly reflected light and the diffusely reflected light increase or decrease according to the density of the subject 1. However, since the direction of the regularly reflected light changes due to the surface concavo-convex defect and since the received amount of the light by the CCD camera extremely changes, it is desirable to receive only the scattered light. Therefore, the CCD camera 13 is located in a position not to receive the light regularly reflected from the subject 1 to eliminate the influence of the change of the light amount due to the surface concavo-convex defect, and only the change of the scattered light due to the blocky defect is photographed.

A normal surface image photographed by the CCD camera 13 has almost uniform density. However, when there is a part which is denser or paler than a normal part, there is supposed to be a blocky defect. The total value of the average value of the photographed image density and a predetermined density difference value within a normal limit is a threshold, and is binarized. As for the blocky defect, there is a case where the density is denser and a case where the density is paler than a normal part. Namely, the binarizing is needed for both the average density plus density difference and the average density minus density difference.

One of these two binarized images has a normal part 1 (white) and a defective part 0 (black), and the other has a normal part 0 (black) and a defective part 1 (white). A decision to pass or fail can be made whether there is image data 0 when the normal part is 1 (white) and the defective part is 0 (black), and whether there is image data 1 when the normal part is 0 (black) and the defective part is 1 (white).

Accordingly, the embodiment of the defect detector of the present invention for an electrophotographic photoreceptor can make a judgement with a suitable algorithm to respective patterns.

In the embodiment of the defect defector in FIG. 1, a distance of a defect, extracted from an image photographed by the optical system emitting coaxial incident-light and an image photographed by the optical system emitting inclined light, is computed in the axial direction of the subject 1. When the subject 1 has a cylindrical form as the embodiment in FIG. 1, the number of defects are approximately several in a subject. Therefore, the defects can be supposed to be the same defects when the positions are the same in the axial direction of the cylinder. When the surface concavo-convex defect and the blocky color defect are combined and an identification has to be made in consideration of both the defects, another judgement standard, besides judgement standards of the surface concavo-convex defect and blocky defect, can be applied. When the subject 1 is belt-shaped, a defect location is computed in the direction of the belt width with respect to each unit length in the longitudinal direction of the belt and compared. At this time, the image photographed by the optical system using coaxial incident-light is computed to determine the location of the defect and the location is memorized in the memory, and the image photographed by the optical system using inclined light is computed to determine the location of the defect and the location is memorized in the memory. The locations memorized in the memory are both compared to identify the kinds of defects.

Further, when the physical relationship of the defects on the images photographed by the two optical systems has to be completely identified, the two one-dimensional CCD cameras 10 and 13 are located such that they have the same visual field first. Next, the one-dimensional CCD cameras 10 and 13 are located above the subject 1 at an angle of 180° and the photographing is started with the two cameras having different photographing timing for 0.5 sec. Thus, it becomes easy to compare the location of the defect on the two images and to identify whether the defect is a concavo-convex defect or a blocky defect alone, or a combined defect.

A judging method of a defect which has to be identified in consideration of both the defects will be explained.

The surface concavo-convex defect is determined to pass or fail based on, for example, the maximum length or the area of the defective part from the facing viewpoint. On the other hand, the blocky defect is determined to pass or fail based on the amount of density difference between a normal part and the defective part. However, when the surface concavo-convex defect and the blocky defect exist on the same location, i.e., when they are combined, a damage to a product is larger than that by a mono-defect and there is a case where the judgement standard has to be more severe.

When the judgement standard has to be more severe, the concavo-convex defective part is extracted by binarizing from the above-mentioned image photographed with the coaxial incident-light to compute the location of the defective part in the photographed image first. Next, the blocky defective part is extracted by binarizing from the above-mentioned image photographed with the inclined light to compute the location of the defective part in the photographed image. Then, when other coordinate data are within a predetermined range of each computed coordinate, the defect may be a combined one and a more severe threshold is applied to determine whether to pass or fail. When the coordinate data are not within the range, a modest threshold is applied to determine whether to pass or fail.

As a matter of course, all coordinates of each extracted defect data do not have to be computed and compared. As for adjacent defect data, the average value of the coordinates and a coordinate of the gravity point may be used to compare.

In addition, when the one-dimensional CCD camera 13 is in a position to receive the regularly reflected light, it receives the light regularly reflected from the surface concavo-convex defect of the subject 1 even when the inclined light is emitted thereto and an excessive judgement is occasionally made. Therefore, the locations of the one-dimensional CCD camera 13 and the linear light source 11 are arranged such that the regularly reflected light does not enter the one-dimensional CCD camera 13. Accordingly, only a blocky color defect can be photographed and the blocky color defect can be exactly identified.

Figure 2:
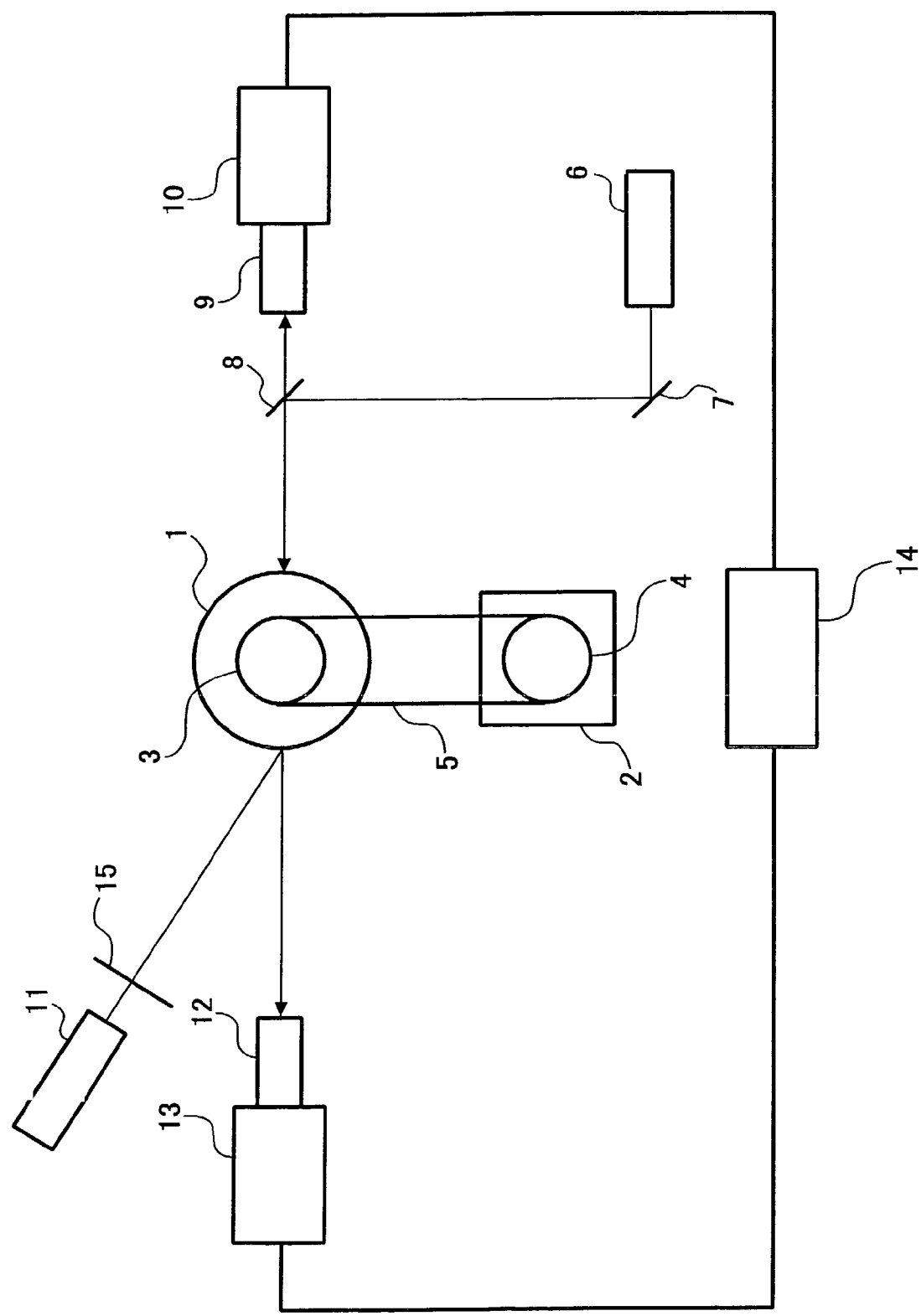
FIG. 2 is a schematic view illustrating another embodiment of the defect detector of the present invention.

FIG. 2 is a schematic view illustrating another embodiment of the defect detector of the present invention. In FIG. 2, the same numerals as those of FIG. 1 represent the same compositions as in FIG. 1. As a different composition, a lacteous acrylic resin board is arranged between the linear light source 11 and the subject 1 as a diffusion board 15. The light emitted from the linear light source 11 is scattered by the diffusion board 15 and irradiated to the subject 1 which is axially rotating by the rotating drive of the drive unit 2. Accordingly, the light is uniformly irradiated to the subject 1 and a uniform image can be photographed to exactly identify change of density of the blocky color defect. In addition, in this embodiment, a lacteous acrylic resin board is used, however, the board is not limited thereto and a red transparent acrylic-resin board may be equipped. By irradiating the red light to the subject 1, the contrast of the photographed image can be increased and the density difference between the normal part and the defective part of the blocky color defect can be emphasized, and it is easier to extract the defect. An orange color or a yellow transparent acrylic-resin board can also increase the contrast. Further, the electrophotographic photoreceptor used as the subject 1 in this embodiment has a green color because a white undercoat layer, a blue-green charge generation layer overlying thereon and a yellowish transparent charge transport layer overlying thereon are coated on an aluminium substrate. Therefore, a green transparent acrylic-resin board may be used as the above-mentioned diffusion board 15. By irradiating light having a similar color to the subject 1, such a blocky defect as has different colors for the normal part and the defective part, because the color of the undercoat layer is revealed due to a deficit of the charge generation layer, can be easily photographed. In addition, the binarization when the defect is extracted can be easily performed.

In FIGS. 1 and 2, a subject-side telecentric lens is used as the photo acceptance lens 9 for the optical system using coaxial incident-light. Even when the distance between the subject 1 and the photo acceptance lens 9 changes due to a deflection of the subject 1, the scale of the defect can be uniformly photographed by the telecentric lens and the scale of the concavo-convex defect can be exactly identified.

Figure 3:
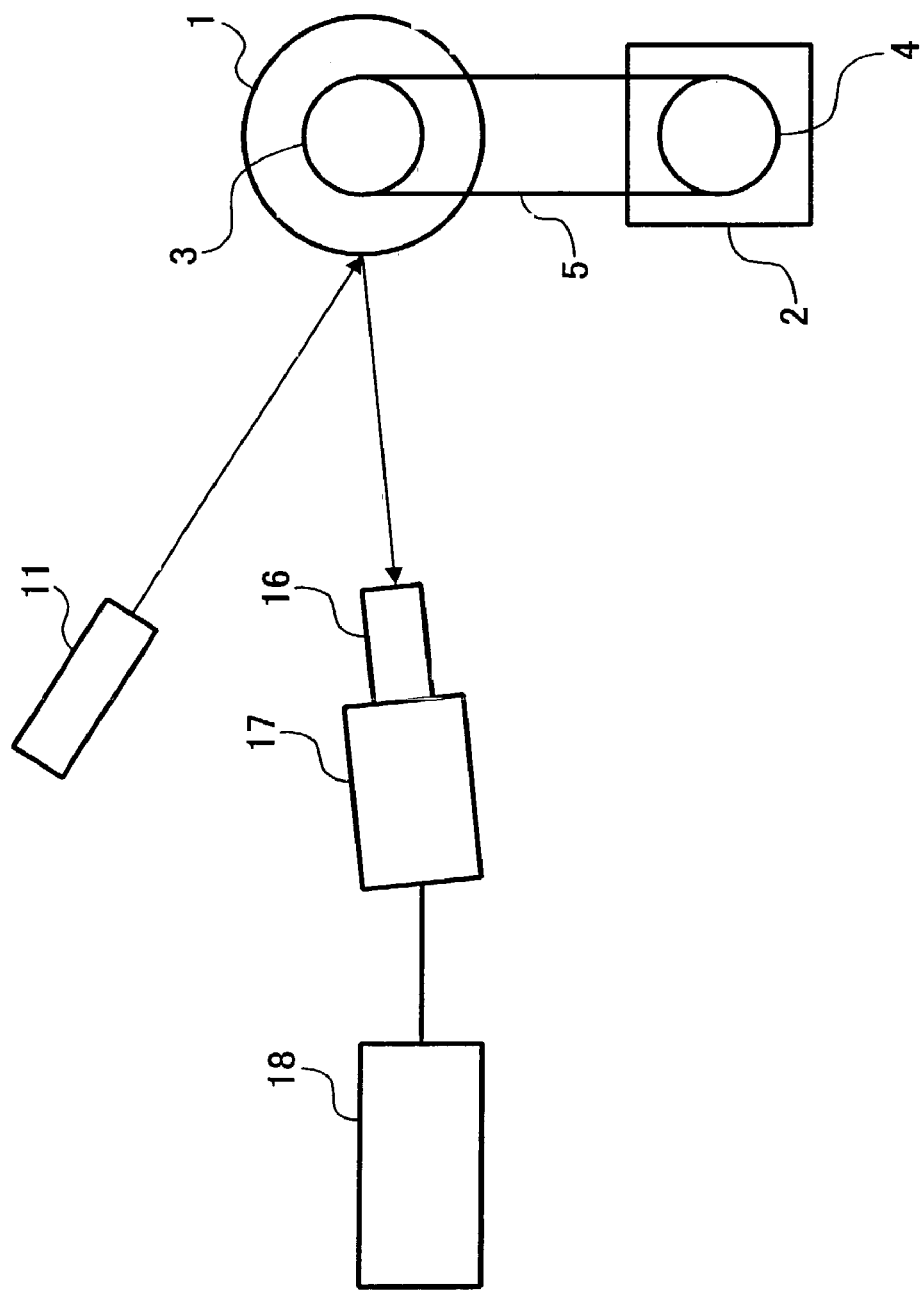
FIG. 3 is a schematic view illustrating a comparative embodiment of a defect detector.

FIG. 3 is a schematic view illustrating a comparative embodiment of a defect detector. In FIG. 3, the same numerals as those of FIG. 1 represent the same compositions as in FIG. 1. In FIG. 3, light from the linear light source 11 arranged in a position inclined at a predetermined angle in a normal direction of the subject 1 is irradiated thereto. The scattered light at the subject 1, which is axially rotating by the rotating drive of the drive unit 2, is received by a monochrome 256 tone one-dimensional CCD camera 17 to change the light to an electrical signal through a photo acceptance lens 16 arranged in a position to receive the scattered light. The electrical signal, changed by the one-dimensional CCD camera 17, is transferred to a computer 18 in which the electrical signal, transferred from the one-dimensional CCD camera 17, is compared with a predetermined threshold and binarized to identify whether there is a defect and to determine whether to pass or fail using an algorithm for making the judgement. The photo acceptance lens 16 and the one-dimensional CCD camera 17 are arranged in a position to receive both the regularly reflected light and the scattered light from the subject 1 such that both the concavo-convex defect and the blocky defect can be photographed. In the method of this comparative embodiment, since both the concavo-convex defect and the blocky defect are photographed on an image, a threshold to determine whether to pass or fail is set in accordance with the most severe judgement standard and the number of rejected subjects increase.

Figure 4:
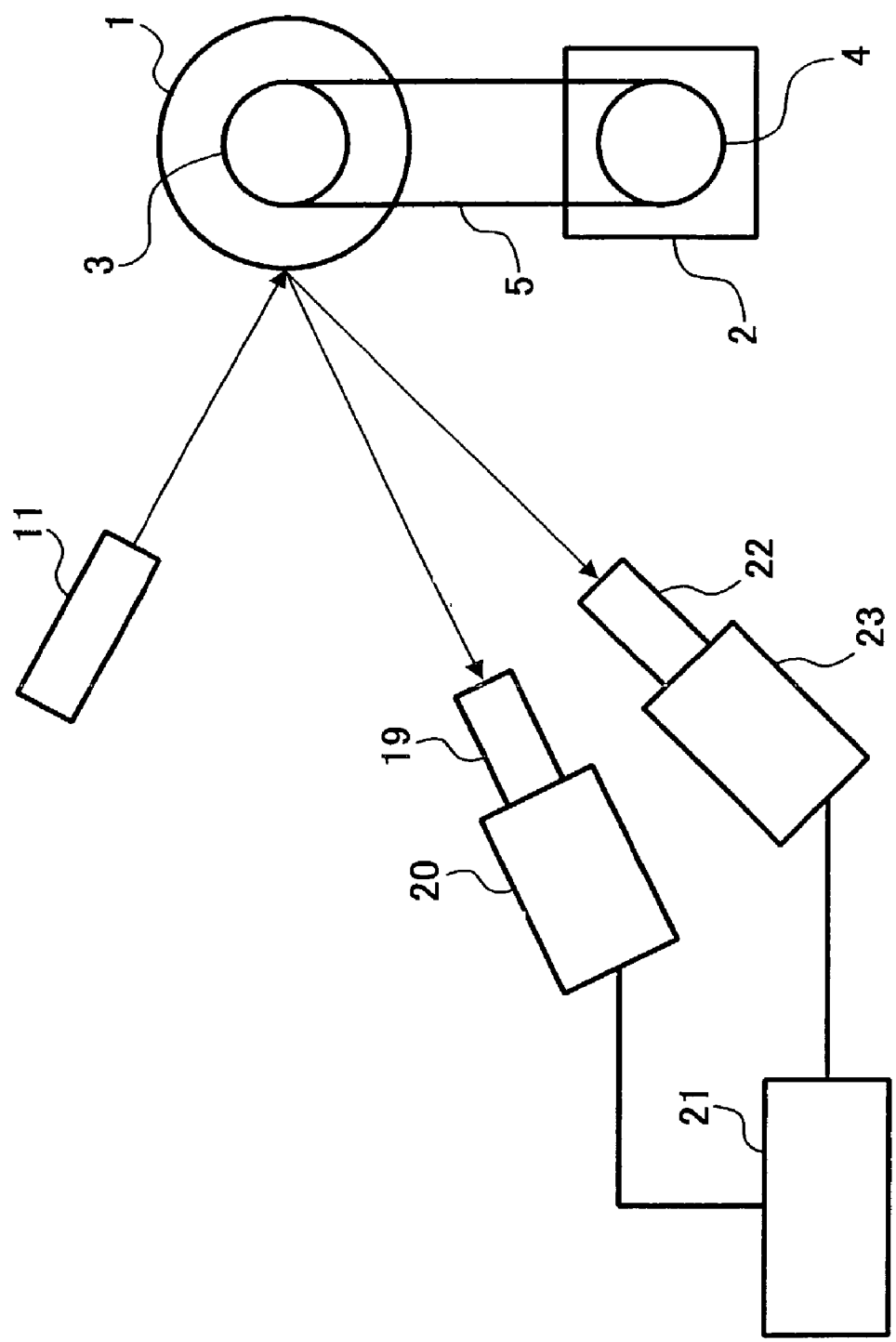
FIG. 4 is a schematic view illustrating another comparative embodiment of a defect detector.

FIG. 4 is a schematic view illustrating another comparative embodiment of a defect detector. In FIG. 4, the same numerals as those of FIG. 1 represent the same compositions as in FIG. 1. In FIG. 4, light from the linear light source 11, which is arranged in a position inclined at a predetermined angle in a normal direction of the subject 1, is irradiated thereto. The regularly reflected light from the subject 1, which is axially rotating by the rotating drive of the drive unit 2, is received by a monochrome 256 tone one-dimensional CCD camera 20 to change the light to an electrical signal through a photo acceptance lens 19 arranged in a position to receive the regularly reflected light. The electrical signal, changed by the one-dimensional CCD camera 20, is transferred to a computer 21. In addition, the scattered light at the subject 1, which is axially rotating by the rotating drive of the drive unit 2, is received by a monochrome 256 tone one-dimensional CCD camera 23 to change the light to an electrical signal through a photo acceptance lens 22 arranged in a position to receive the scattered light. The electrical signal, changed by the one-dimensional CCD camera 23, is transferred to the computer 21. The electrical signals, transferred from the one-dimensional CCD cameras 20 and 23, are compared with a predetermined threshold respectively and binarized to identify whether there is a defect and to determine whether to pass or fail using an algorithm for making the judgement. In the method of this comparative embodiment, photographing is performed twice and detecting time is twice as long as the other embodiments. Further, since the distance between the subject 1 and the photo acceptance lens 22 has to be lengthened because the two cameras have to be set apart to prevent the mutual interference, the image resolution deteriorates.

The above-mentioned embodiments of the present invention are provided for the purpose of illustration only and are not intended to be limiting.

Having now fully described the invention, it will be apparent to one of ordinary skill in the art that many changes and modifications can be made thereto without departing from the spirit and scope of the invention as set forth therein.

What is claimed as new and desired to be secured by Letters Patent of the United States is:

1. A defect detector, comprising:
    a first optical system including:
        a first light source configured to irradiate a surface of a subject with coaxial incident-light while scanning the subject, and
        a first imaging device configured to receive light regularly reflecting from the subject and change the light to a first electrical signal to form a first electrical image;
    a second optical system including:
        a second light source configured to irradiate the surface of the subject with inclined light while scanning the subject, and
        a second imaging device configured to receive light scattered at the subject and to change the light to a second electrical signal to form a second electrical image, wherein the inclined light of the second light source does not meet the coaxial incident-light of the first light source;
    a computer configured to compare the first electrical signal with a predetermined first threshold to detect a concavo-convex defect on the surface of the subject, and to compare the second electrical signal with a predetermined second threshold to detect a blocky color defect on the surface of the subject; and
    a storage device, wherein
    the computer is further configured to process the first electrical image to determine a first position of the concavo-convex defect and the second electrical image to determine a second position of the blocky color defect,
    the computer is further configured to store the first and second positions in the storage device, and
    the computer is further configured to compare the first position with the second position, and when the first and the second positions are the same, the computer is configured to compare the first electrical signal with a predetermined third threshold to detect the concavo-convex defect and the second electrical signal with a predetermined fourth threshold to detect the blocky color defect.

2. The defect detector of claim 1, wherein the computer is further configured to process the first and second electrical images while an area of the surface of the subject photographed in the first electrical image and an area photographed in the second electrical image are synchronized.

3. The defect detector of claim 1, wherein the second imaging device is located so as not to receive the light regularly reflecting from the subject.

4. The defect detector of claim 1, wherein the second optical system further comprises:
    a diffusion board located on a light path from the second light source to the subject.

5. The defect detector of claim 1, wherein the second optical system further comprises:
    a color filter located on a light path from the second light source to the subject.

6. The defect detector of claim 5, wherein the color filter comprises:
    a color similar to a color of the subject.

7. The defect detector of claim 1, wherein the first imaging device further comprises:

a telecentric lens configured to collect light regularly reflecting from the subject.

8. The defect detector of claim 1, wherein said surface is a cylindrical surface.

9. A method of detecting a defect, comprising:
irradiating a surface of a subject with coaxial incident-light;
receiving light regularly reflecting from the surface of the subject;
changing the light regularly reflecting from the surface of the subject to a first electrical signal to form a first electrical image;
comparing the first electrical signal with a first threshold to detect a concavo-convex defect;
irradiating the surface of the subject with inclined light;
receiving light scattered at the surface of the subject;
changing the light scattered at the surface of the subject to a second electrical signal to form a second electrical signal;
comparing the second electrical signal with a second threshold to detect a blocky defect; and
processing the first electrical image to determine a first position of the concavo-convex defect and the second electrical image to determine a second position of the blocky color defect,
wherein when the first and second positions are the same, the method further comprises:
comparing the first electrical signal with a predetermined third threshold to detect the concavo-convex defect; and
comparing the second electrical signal with a predetermined fourth threshold to detect the blocky color defect.

10. The method of claim 9, wherein said surface is a cylindrical surface.

* * * * *